United States Patent [19]

Tanei et al.

[11] 4,118,779

[45] Oct. 3, 1978

[54] APPARATUS AND PROCESS FOR DETERMINATION OF OIL CONTENT IN DEBALLASTING WATER AND WASH WATER DISCHARGED FROM A TANKER

[75] Inventors: Fumio Tanei, Takatsuki; Toshiaki Ikeda, Otsu, both of Japan

[73] Assignee: Horiba, Ltd., Kyoto, Japan

[21] Appl. No.: 713,686

[22] Filed: Aug. 12, 1976

[30] Foreign Application Priority Data

Sep. 8, 1975 [JP] Japan .................................. 50-109289
Sep. 8, 1975 [JP] Japan .................................. 50-109290

[51] Int. Cl.$^2$ .......................... G01N 7/06; G01N 15/00
[52] U.S. Cl. ..................................... 364/509; 73/61 R; 364/497
[58] Field of Search ...................... 235/151.3, 151.35; 73/53, 61 R, 61.1 R, 195, 198; 114/121, 125; 222/56, 59, 71

[56] References Cited

U.S. PATENT DOCUMENTS

| | | | |
|---|---|---|---|
| 3,167,949 | 2/1965 | Stenzel et al. | 73/61.1 R |
| 3,643,507 | 2/1972 | Garrett | 73/61.1 R |
| 3,913,384 | 10/1975 | Furuya et al. | 73/53 |
| 3,924,449 | 12/1975 | Moreau et al. | 73/61.1 R |
| 3,974,940 | 8/1976 | Bartik | 235/151.35 |
| 3,985,020 | 10/1976 | Moreau | 73/61.1 R |

*Primary Examiner*—Malcolm A. Morrison
*Assistant Examiner*—Errol A. Krass

*Attorney, Agent, or Firm*—McNenny, Pearne, Gordon, Gail, Dickinson & Schiller

[57] ABSTRACT

A technique for accurate determination is provided which allows, at any point of navigation of a tanker and regardless of variation in the velocity of the tanker, the determination of the oil content in deballasting water and tank cleaning water that has been discharged during the navigation of a range extending from said point of navigation to another point with a given distance backward of said point. The technique comprises the determination of an instantaneous rate of discharge of oil content based on the concentration of oil and the quantity of water discharged within a given period of time, thereby obtaining the quantity of oil discharged within a given distance up to the present time as well as an incremental quantity of oil discharged in the period of time that the tanker was traveling a predetermined distance, and use of the thus obtained signals of discharged quantity for recording or control of discharge of deballasting water and tank cleaning water. According to this method, the condition (4) specified by the IMCO as a standard for regulation of discharge of deballasting water and tank cleaning water from a tanker is fully satisfied, and steady navigation of the vessel is made possible. The method uses a practically simple sensing system and process of mathematical calculations, thus obviating a sophisticated computer of the kind heretofore required.

11 Claims, 9 Drawing Figures

PRIOR ART.

APPARATUS AND PROCESS FOR DETERMINATION OF OIL CONTENT IN DEBALLASTING WATER AND WASH WATER DISCHARGED FROM A TANKER

BACKGROUND OF THE INVENTION:

This invention relates to a method and an apparatus which allows, at any point of navigation of a tanker and regardless of variation in the velocity of the tanker, the determination of the oil content in deballasting water and tank cleaning water that has been discharged during the navigation of a distance or range extending from said point of navigation to another point with a given distance backward thereof. Both at national and international levels, the importance is being recognized of laying down regulations for preventing marine pollution. According to the regulations concluded by the Inter-Governmental Marine Consultative Organization (IMCO), which is the specialized agency of the United Nations, all discharge into the sea of deballasting water and tank cleaning water from tankers is prohibited except when all the following conditions are satisfied:

(1) The tanker is not within a special area;
(2) The tanker is more than 50 nautical miles from the base line of the territorial waters of the nearest nation;
(3) The tanker is proceeding en route;
(4) The instantaneous rate of discharge of oil content in deballasting water and tank cleaning water does not exceed 60 liters per nautical mile (the instantaneous rate of discharge of oil content is the total quantity of oil discharged per hour divided by the velocity of the tanker in terms of "knot" and this is hereunder referred to as an incremental quantity of oil discharged);
(5) The total quantity of oil discharged does not exceed for existing tankers 1/15,000 of the total cargo carrying capacity of the vessel, and for new tankers 1/30,000 of the total cargo carrying capacity of the vessel; and
(6) The tanker has, in operation, oil discharge monitoring and control systems.

This invention relates to a method and an apparatus for determination of the oil content in deballasting water or cleaning water discharged from a travelling tanker, thereby controlling the discharge of oil in such a manner that the condition (4) mentioned above may be satisfied. Conventionally, the quantity of oil content discharged is controlled by first multiplying an instantaneous oil concentration p by an instantaneous flow amount q and dividing the product by the velocity of an associated tanker to obtain an incremental quantity of oil discharged $L + pg/V$ (the instantaneous rate of oil discharged as defined in the condition (4)) and then stopping the discharge of deballasting water and washing water from the tanker when said value exceeds a predetermined level (for example, 60 liters/nautical mile as mentioned earlier). But in view of the nature of oil (it is easily deposited on the sampling line), this method is not acceptable. To be more specific, once concentrated oil is deposited on the sampling line, instantaneous determination gives a value $L = pg/V$ that is greater than the allowable limit, and then this requires the discharge of deballasting water and cleaning water to be stopped, but then $q$ becomes zero to give $L=0$ that is smaller than the allowable limit, and this enables the deballasting water and cleaning water to be discharged again. However, the oil concentration is still high enough to make L greater than the allowable limit and therefore the discharge is stopped again, whereupon an oscillation or chattering effect occurs to cause a failure in control of the discharging operation.

According to another method that has been devised to overcome this defect, an oil discharge rate L for a predetermined distance (for instance, a nautical mile) is determined by the following formula, with the velocity V of a tanker and the distance $l$ being constant and an instantaneous concentration of oil p and an instantaneous flow rate $q$ being actually measured:

$$L = \int_0^t pg\, dt$$

(wherein V and $l$ are constant in $l/V = t$, and therefore, t is constant). However, this method requires the factors to be reset upon every lapse of the time "t" required for travelling the predetermined distance (for instance, one nautical mile). For this reason, determination is also required at places (or times) other than the set places (or times) of "$t_1$" and "$t_2$" (see FIG. 9). In addition, it is technically difficult to maintain the navigating velocity of a vessel constant.

Such drawbacks inherent in the conventional methods for controlling the discharge of oil content are eliminated by the method and apparatus of the present invention. In the pages that follow, some embodiments of this invention will be described in detail based on the attached drawings.

DESCRIPTION OF THE PREFERRED EMBODIMENTS

Figure 9:
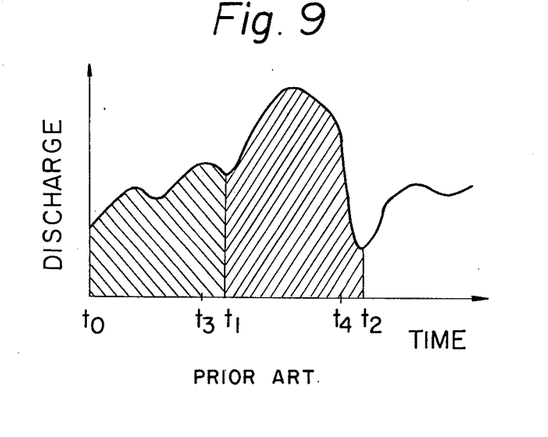
FIG. 9 illustrates the conventional method.

According to the conventional method, a determination of an oil discharge rate per nautical mile is required at places or times other than the set places or times of "$t_1$" and "$t_2$" shown in FIG. 9. Needless to say, this method makes it difficult to determine the amount of oil discharged within a distance of one nautical mile backward from the set places or times, for instance, a distance or time between $t_3$ and $t_4$.

Figure 1:
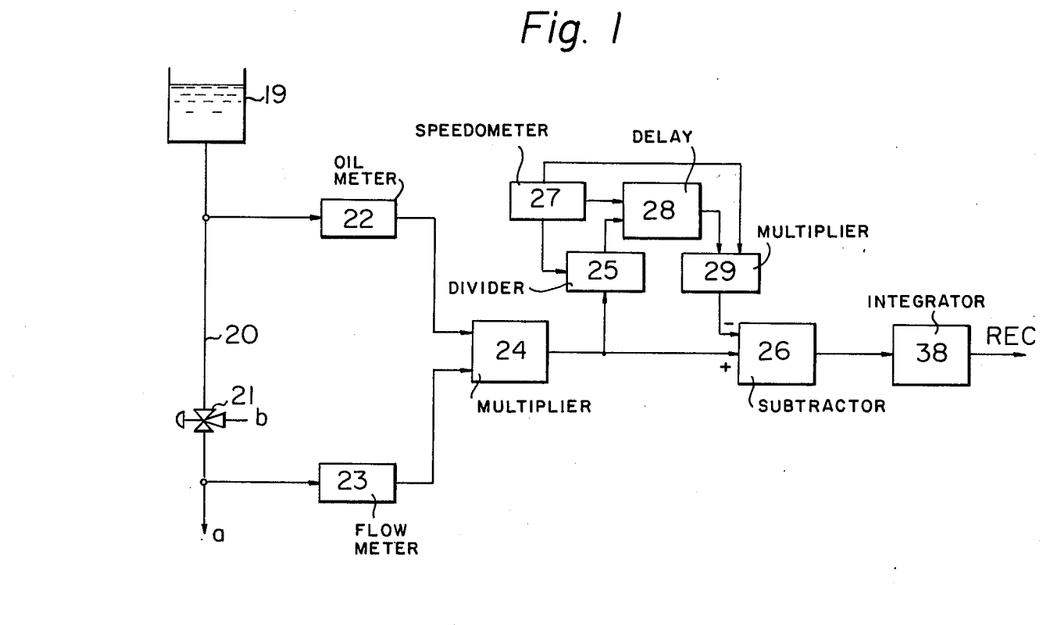
FIG. 1 shows one example of the apparatus used for the working of the process of this invention.

In FIG. 1, deballasting water and cleaning water separated from oil in a slop tank 19 flows through a discharge pipe 20 to be discharged into the sea via a switch valve 21 (refer to the arrow "a").

The oil content in the water discharged along the pipe 20 is determined by an oil meter 22, while the flow rate of the water is determined by a flow meter 23.

Signal from the oil meter 22 is multiplied by that from the flow meter 23 in a multiplier 24 to obtain an instantaneous rate of discharge of oil content. When we write Pt and qt for an instantaneous concentration of oil content and an instantaneous flow rate at the time of "$t$", respectively, an instantaneous rate of discharge of oil content at the time of "$t$" is:

$$Lt = Pt \times qt \qquad (1)$$

Signal from the multiplier 24 is provided to the unreverting input of a divider 25 and a subtractor 26.

In the divider 25 whereto an output signal, a velocity of "V", from a speedometer 27 that measures the navigating velocity of the vessel is provided, said instantaneous rate of discharge of oil content Lt is converted to an incremental quantity of oil discharged Ls based on the formula:

$$Ls = Lt/V \qquad (2)$$

The incremental quantity of oil discharged Ls is the oil content that has been discharged from a tanker within an incremental distance or a small given distance of "S" travelled by the tanker and has the same meaning as that of the instantaneous rate of discharge of oil content defined in the condition (4) above. This value is obtained by dividing the instantaneous rate of discharge of oil content Lt by the velocity at any instant. An output signal from the divider 25, i.e. the incremental quantity of oil discharged Ls, is provided to a delay or delay circuit 28.

The delay 28 delays the incremental quantity of oil discharged for a period of time required for the tanker to travel a given distance, for example, 1 nautical mile, and then it provides the signal to a multiplier 29. One example of its construction is indicated in FIG. 2 (any delay that achieves the same function, for example, a delay which employs a recording tape, will do).

Figure 2:
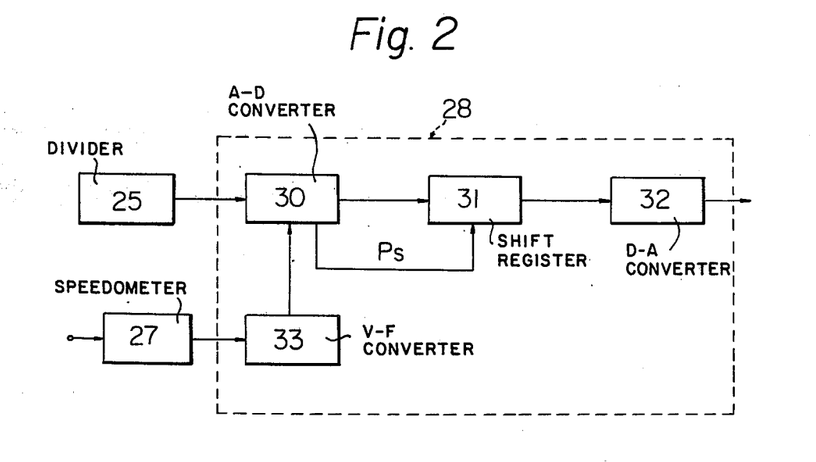
FIG. 2 shows more specifically an essential part of FIG. 1.

Referring to FIG. 2, 27 is a speedometer that measures the navigating velocity of the tanker; 33 is a V-F converter which converts a velocity signal from the speedometer 27 into a pulse signal having a frequency that corresponds to the velocity; 30 is an A-D converter which divides the output signal from the divider 25, i.e. the analog signal that indicates an incremental quantity of oil discharged into a digital signal in synchronization with the pulse signal from the V-F converter 33; 31 is a shift register which memorizes the digital signal from the A-D converter 30 in the order of division, shifts said digital signal by a shift pulse Ps synchronized with said pulse signal, and outputs said digital signal in response to a given number of such shift pulses; and 32 is a D-A converter which reproduces the initial signal of the incremental quantity of oil discharged by converting to an analog signal the digital signal outputted from the shift register 31.

In connection with the delay 28, if the navigating velocity of a tanker "V" is great, the frequency of a pulse signal from the V-F converter 33 as well as that of a shift pulse Ps is high. Therefore, the period of time (delay time) from the input of the digital signal indicating the incremental quantity of oil discharged to the shift register 31 to the output of the same therefrom is short. Conversely, a low speed of the navigating vessel results in a long delay time (this means that regardless of the velocity of the tanker, the delay 28 delays the signal for a period of time required for the vessel to travel a predetermined distance). For this reason, by selecting a suitable memory capacity of the shift register 31, the delay time can be set at a level of the time that is always required for the vessel to travel a predetermined distance, for example, one nautical mile. To state more specifically, when we write "$l$" for a predetermined distance (for instance, one nautical mile specified in the condition 4 set forth above), and "V($t$)" for the navigating velocity at any moment, the delay time of $t_2 - t_1$ is calculated from the formula:

$$l = \int_{t_1}^{t_2} V(t)\, dt \qquad (3)$$

(wherein $t_2$ represents the time at the present location while $t_1$ represents the past time when the tanker was navigating in a place with a distance of "$l$" backward from said present location.)

The output signal from the delay 28 at the present time of $t_2$ is the quantity of oil "$Ls_1$" discharged within a small given distance when the tanker was navigating a length of time of "$t_2 - t_1$" ago, that is, when it was navigating in a place with a distance of "$l$" backward from the present location. The value of $Ls_1$ is given by the formula of:

$$Ls_1 = \frac{Pt_1 \times qt_1}{V_1} \qquad (4)$$

(wherein $Pt_1$ is an instantaneous concentration of oil at the time of $t_1$, $qt_1$ is a flow rate of discharged water at the time of $t_1$, and $V_1$ is a navigating speed at the time of $t_1$).

The output signal from the delay 28, namely, the incremental quantity of oil discharged $Ls_1$, is inputted to the multiplier 29, wherein together with the input of the output signal from the speedometer 27, i.e. the velocity of $V_2$ at the present time of $t_2$, it is converted to an instantaneous rate of discharge of oil content $Lt_1$, at the present time of $V_2$ based on the formula of:

$$Lt_{1'} = \frac{Lt_1}{V_1} \times V_2 \qquad (5)$$

As the formula indicates, the instantaneous rate of discharge of oil content $Lt_1$ at the time of $t_1$ when the tanker was navigating at a velocity of $V_1$ is corrected by conversion to $Lt_{1'}$, that indicates an instantaneous rate of discharge of oil at the present time of $t_2$ when the tanker is navigating at a different velocity. Without this correction, a difference of velocity between the time of $t_1$ and $t_2$ may result in an error (in fact, a tanker seldom navigates at a constant speed; it often changes speed).

The output signal from the multiplier 29 is provided to the reverting input of the subractor 26, wherein the formula (5) is subtracted from the formula (1) to obtain the difference L between the instantaneous rate of discharge of oil content $Lt_2$ at the present time of $t_2$ and the instantaneous rate of discharge of oil content $Lt_1$, at the time of $t_1$:

$$L = Pt_2 \times qt_2 - Pt_1 \times qt_1 \times (V_2/V_1) \qquad (6)$$

The obtained value L is then inputted to an integrator 38 in the next stage.

The integrator 38 integrates the differential content of oil discharged at each point up to the present time of $t_2$ inclusive to obtain an integral value of Lin represented by the formula:

$$Lin = \int_o^t Ldt = \int_o^{t_2} P \times qdt - \int_o^{t_1} P \times qdt \qquad (7)$$

$$= \int_{t_1}^{t_2} P \times qdt$$

Figure 3:
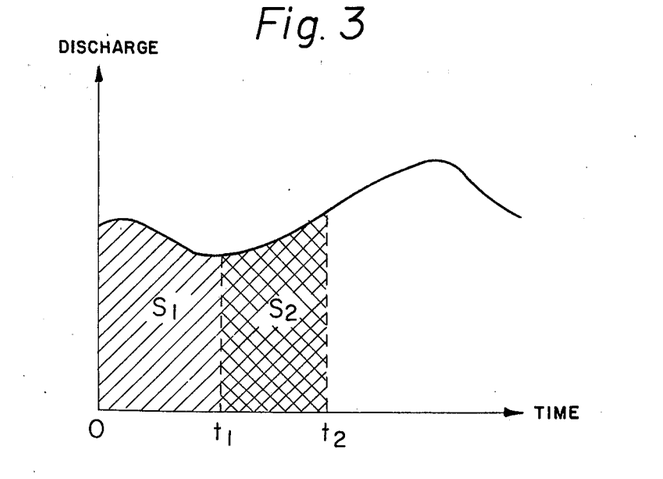
FIG. 3 illustrates the process of this invention.

Being the quantity of oil discharged in a time length from the start of discharge to $t_1$, $$\int_o^{t_1} P \times qdt$$

in the formula is an integral value of the signal delayed by the delay 28 and it corresponds to $S_1$ indicated in the graph of FIG. 3 that illustrates the quantity of oil discharged. On the other hand, $$\int_o^{t_2} P \times qdt$$

corresponds to $S_1 + S_2$ in the same figure. Accordingly, the integral value "Lin" given by the difference of the two corresponds to $S_2$ in said figure, indicating the total amount of oil discharged within a period from $t_1$ to the present time of $t_2$, that is, the content of oil discharged from the tanker within a predetermined distance of "$l$" and determined at the time of $t_2$.

In the embodiment described above, the integrator 38 is placed next to (or on the output side of) the subtractor 26. Instead, two integrators may be placed before (or on the input side of) the subtractor to effect integration prior to subtraction. Alternatively, the subtractor 26 may be replaced by an adder, with a phase converter being placed between this adder and the multiplier 29. As another modification, an adder-integrator may be substituted for the subtractor 26 and the integrator 38, with a phase converter being placed between the multiplier 29 and the adder-integrator.

Figure 4:
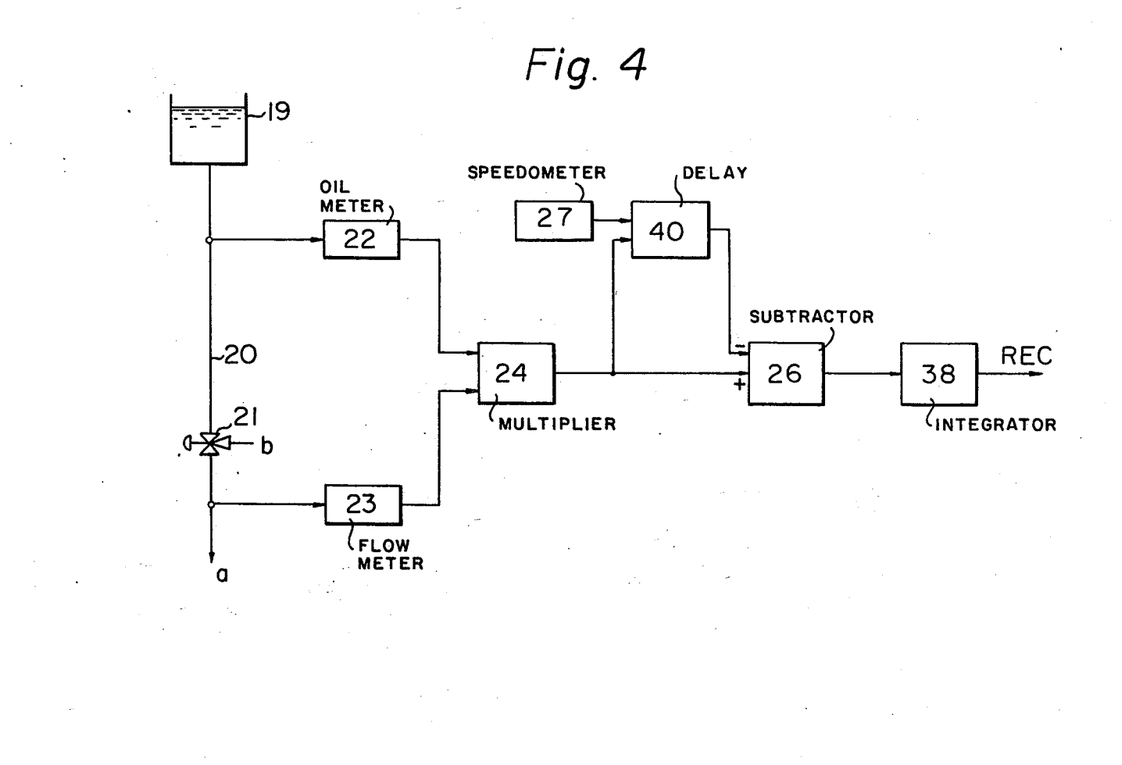
FIG. 4 shows another example of the apparatus used for the working of the process of this invention.
Figure 5:
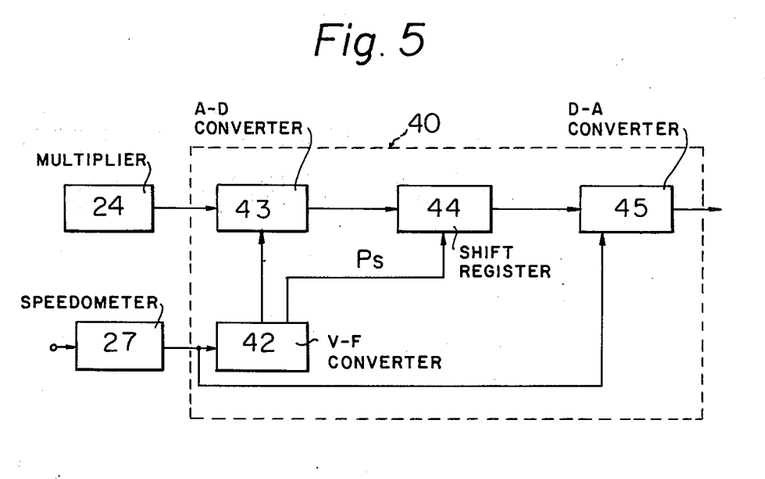
FIG. 5 describes the construction of an essential part of FIG. 4.
Figure 6:
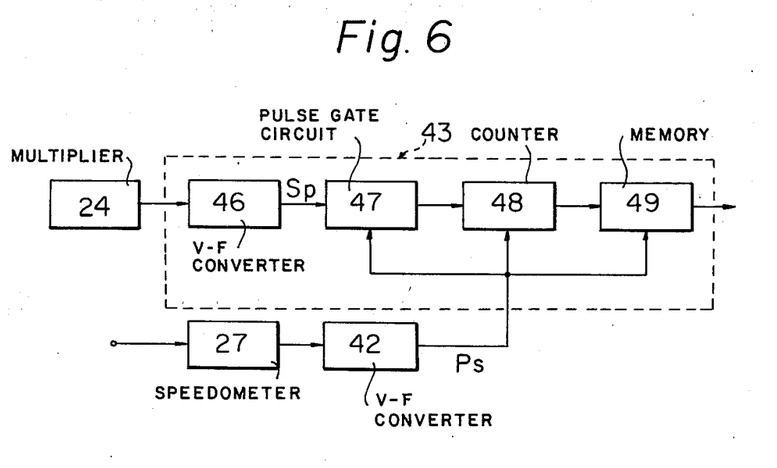
FIG. 6 is a more specific description of an essential part of FIG. 5.

FIGS. 4 to 6 show another embodiment of the process of this invention. According to this embodiment, operations performed by the divider 25 and the multiplier 29 in the above described embodiment are performed by a delay 40. The following explanation is only directed to the delay 40 since the other components are the same as those set forth in FIG. 1.

One example of the construction of the delay is illustrated in FIG. 5. Referring to the figure, 27 is a speedometer which measures the navigating velocity of a tanker; 42 is a V-F converter which converts the velocity signal from the speedometer 27 to a pulse signal having a frequency that corresponds to the velocity; 43 is an A-D converter which converts to a digital signal the output signal from the multiplier 24, i.e. the analog signal indicating an instantaneous rate of discharge of oil content, by dividing the same with a velocity of V in synchronization with the pulse signal from the V-F converter 42 (the details of the A-D converter that is capable of the operation of division will be given later); 44 is a shift register which memorizes the digital signal from the A-D converter in the order of division, shifts said digital signal by a shift pulse P$s$ synchronized with the pulse signal, and outputs said digital signal in response to a given number of such shift pulses; and 45 is a D-A converter capable of the operation of multiplication which reproduces the initial signal of the instantaneous rate of discharge of oil content by conversion to an analog signal of the digital signal from the output of the shift register 44 as a result of multipication of said digital signal by a navigating velocity of V (the velocity $V_2$ at the present location).

An example of the construction of the A-D converter 43 capable of the operation of division is illustrated in FIG. 6. Referring to the figure, 27 is a speedometer which measures the navigating velocity of a tanker; 42 is a V-F converter which converts the speed signal from the speedometer 27 to a pulse signal having a frequency that corresponds to the velocity; 46 is a V-F converter which converts the output signal from the multiplier 24, i.e. an analog signal indicating an instantaneous rate of discharge of oil content, to a pulse signal having a frequency that corresponds to the output; 47 is a pulse gate circuit which opens the gate in synchronization with the pulse signal from the V-F converter 42; 48 is a counter circuit which is reset in synchronization with the pulse signal from the said V-F converter 42 and counts the number of pulses of the output signal that have passed said pulse gate circuit by the time of resetting; and 49 is a memory which is reset in synchronization with the pulse signal from the V-F converter 42 and memorizes the number counted by said counter circuit 48.

In the construction of the A-D converter 43 illustrated above, when an output signal from the multiplier 24, i.e. the analog signal that indicates an instantaneous rate of discharge of oil content, is inputted to the V-F converter 46, it is converted to a pulse signal Sp having a frequency in proportion to its magnitude, and provided to the pulse gate circuit 47 on the next stage. The gate in the pulse gate circuit 47 is opened and closed by the pulse Ps having a frequency proportional to the navigating velocity of the tanker, and so, the pulse signal Sp passes the circuit 47 within a period when the gate is opened by the pulse Ps, namely, within a duration of one pulse, and is inputted to the counter circuit 48 for counting. The function of the pulse gate circuit 47 through which the pulse signal S$p$ carrying information of an instantaneous rate of discharge of oil content passes within a duration of one pulse Ps that carries information of a navigating velocity is to divide the instantaneous rate of discharge of oil content L$t_1$ by a navigating velocity of $V_1$ at the instant of $t_1$. In the counter circuit 48 on the next stage, information divided by the pulse gate circuit 47, namely an incremental quantity of oil discharged L$s_1$, is counted, and the counts are memorized by the memory 49.

The output pulse signal from the A-D converter 43 is inputted to a shift register 44, wherein it is delayed in the same manner as described in connection with the aforementioned embodiment. The delayed signal is then converted to an analog signal in a D-A converter 45. The D-A converter 45 is capable of operation of multiplication, because instead of a constant voltage applied to ordinary D-A converters, an analog signal indicating a velocity is inputted to this converter. As the delayed signal is subjected to D-A conversion, it is multiplied by a navigating velocity $V_2$ at the instant of $t_2$.

The output signal from the D-A converter 45 is provided to the reverting input of the subtractor 26, wherein it is subtracted from an instantaneous rate of discharge of oil content at the present time of $t_2$ that has been provided to the unreverting input of the subtractor, and integrated in an integrator 38 in the same manner as described before. The thus obtained signal indicating the oil content (the quantity of oil discharged) in the deballasting water or cleaning water that has been discharged during the navigation of a distance or range extending from the present navigation point to another point with a given distance backward thereof is made use of as a signal for indication, recording or control according to the occasion.

Figure 7:
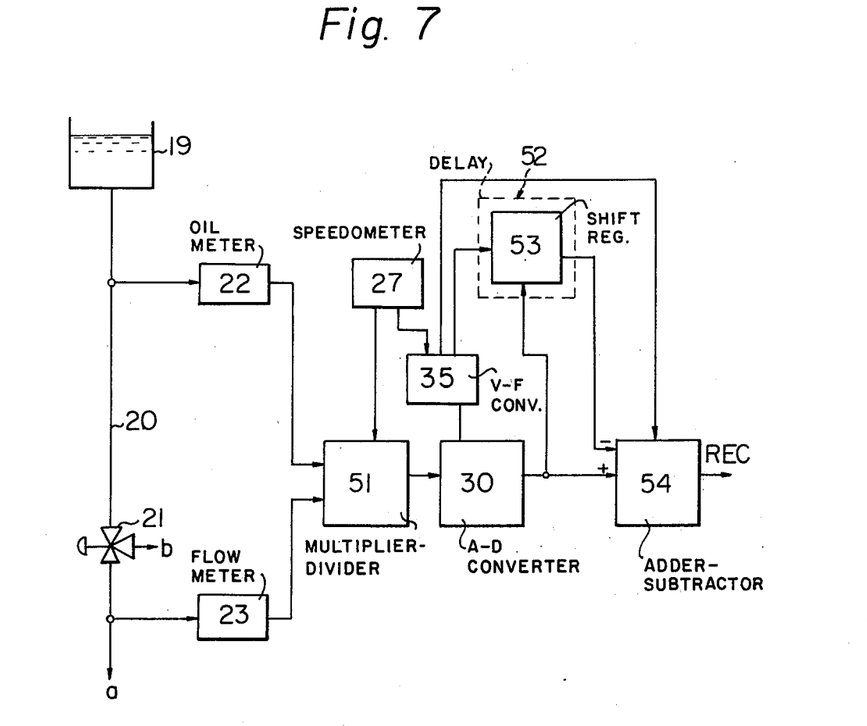
FIG. 7 explains the operation of the second embodiment of this invention according to digital system.

The second embodiment of the process of this invention will be specifically explained according to FIG. 7. Deballasting water or cleaning water separated from oil in a slop tank 19 flows in a discharge pipe 20 and is discharged into the sea through a switch valve 21 (refer to the arrow *a*). As described earlier, the concentration of oil in the water flowing in the pipe 20 is measured by an oil meter 22, while the flow rate of the water is determined by a flow meter 23. The navigating velocity of a tanker is determined by a speedometer 27. The velocity signal is inputted to a multiplier-divider 51 comprising a multiplier connected to a divider, and at the same time, it is inputted to a V-F converter 35 for conversion to a pulse having a frequency corresponding to the velocity. In the multiplier-divider 51, the signal from the oil meter 22 is multiplied by that from the flow meter 23, and the product is divided by the velocity signal to determine an incremental quantity of oil discharged $Ls$, which is then inputted to an A-D converter 30. A digital signal from the A-D converter 30 is provided to the unreverting input of a delay 52 and an adder-subtractor 54.

The delay 52 delays said incremental quantity of oil discharged for a period of time required for the tanker to travel a predetermined distance, for example, one nautical mile, and it then provides the delayed signal to the reverting input of the adder-subtractor 54. One example of a delay achieving such function is a shift register 53. The shift register 53 memorizes the digital signal from the A-D converter 30 in the order of division, shifts said digital signal by a shift pulse $Ps$ synchronized with the output signal from the V-F converter 35, that is, a pulse signal, and outputs said digital signal in response to a given number of shift pulses $Ps$.

The delayed output signal from the delay 52 is provided to the reverting input of the adder-subtractor 54. Being of a construction which consists of an adder and a subtractor, said adder-subtractor 54 subtracts, in response to a pulse signal $Ps$ from the V-F converter 35, the digital signal delayed by said delay 52, that is, an incremental quantity of oil discharged $Ls_1$ at the time preceding the present time of $t_2$ by $t_2 - t_1$, from the digital signal outputted from the A-D converter 30, that is, an incremental quantity of oil discharged $Ls_2$ at the present time of $t_2$:

$$L = Ls_2 - Ls_1 = \frac{Pt_2 \times qt_2}{V_2} - \frac{Pt_1 \times qt_1}{V_1} \tag{8}$$

Subsequently, the subtracted value L at each incremental distance is summed up in response to a pulse signal $Ps$ from the V-F converter 35 to obtain a summed up value R represented by the following formula:

$$R = \sum_{k=0}^{t} L_k = \sum_{k=0}^{t_2} \frac{P_k q_k}{V_k} - \tag{9}$$

-continued
$$\sum_{k=0}^{t_1} \frac{P_k q_k}{V_k} = \sum_{k=t_1}^{t_2} \frac{P_k q_k}{V_k}$$

Referring to this formula, $$\sum_{k=0}^{t_1} \frac{P_k q_k}{P_k}$$

is the quantity of oil discharged within a period from the start of discharge to the time of $t_1$, and corresponds to $S_1$ indicated in the graph of FIG. 3 that illustrates the quantity of oil discharged. On the other hand, $$\sum_{k=0}^{t_2} \frac{P_k q_k}{V_k}$$

corresponds to $S_1 + S_2$ in the same figure. Accordingly, the summed up value R represented by the difference of the two corresponds to $S_2$ in said figure, indicating the total amount of oil discharged within a period from the time of $t_1$ to the present time of $t_2$, or the amount of oil discharged from the tanker travelling a predetermined distance "*l*" that is measured at the time $t_2$.

As described in the foregoing pages, according to the method of this invention, it becomes possible to determine at any point of navigation the oil content (the quantity of oil discharged) in deballasting water and cleaning water that has been discharged during the navigation of a distance or range extending from said point of navigation to another point with a given distance backward thereof. The thus obtained signal indicating the quantity of oil discharged is used for indication, recording or control according to the purpose.

Figure 8:
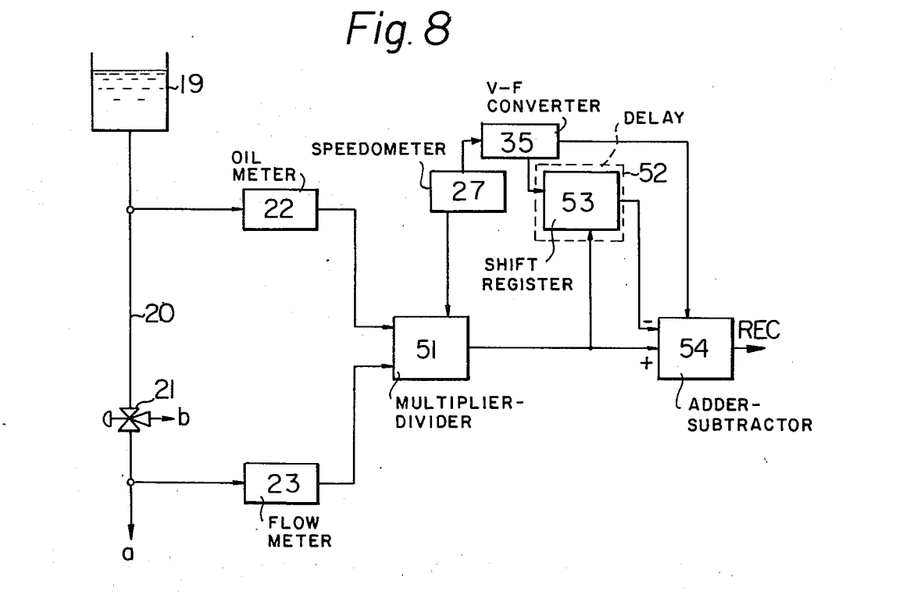
FIG. 8 explains the operation of the third embodiment of this invention according to analog system.

FIG. 8 shows the third embodiment of this invention. The A-D converter 30 shown in FIG. 7 is not used in this embodiment. Instead, an analog signal performs delaying, and an adder-subtractor effects subtraction, followed by addition in response to an output signal from a V-F converter 35, i.e. a pulse signal $Ps$ which indicates the velocity.

In this connection, it should be noted that both in the embodiments of FIGS. 7 and 8, the adder-subtractor 54 may be replaced by a subtractor connected to an adder in series. Further, the A-D converter 30 that is placed next to the multiplier-divider 51 in FIG. 7 may be placed next to the oil meter 22, flow meter 23 and speedometer 27, respectively. A still further modification may be the substitution of a digital multiplier-divider for the analog multiplier-divider 51.

As will be understood from the preceding explanation, the process and apparatus of this invention makes it possible to determine at any point of navigation the oil content (the quantity of oil discharged) in deballasting water and cleaning water that has been discharged during the navigation of a distance extending from said point of navigation to another point with a given distance backward thereof. In addition, the determination of the oil discharged is always accurate regardless of a variation in the velocity of the navigating tanker.

What is claimed is:

1. An apparatus for determining the amount of oil in deballasting water and tank cleaning water that has been discharged from a travelling tanker during the navigation of a distance extending from a point of navigation at a time $t_1$ to another point of navigation at a time $t_2$ within a given distance backward of said another point of navigation, said apparatus comprising:

an oil meter for measuring the concentration of oil in said water at a first time $t_1$ and a second time $t_2$, said oil meter providing a signal indicative of said concentrations;

a flow meter for measuring the flow rate of said water at said first time $t_1$ and said second time $t_2$, said flow meter providing a signal indicative of said flow rates;

a first multiplier for multiplying said concentration signal from said oil meter by said flow rate signal from said flow meter at said times, said first multiplier providing an output signal indicative of the instantaneous rate of discharge of oil at said time $t_1$ and at said time $t_2$;

a first divider for dividing said output signal at said time $t_1$ from said first multiplier by a navigating velocity at said time $t_1$ of said tanker at said time $t_1$ of determining said flow rate and said oil concentration so as to obtain an analog signal indicative of an incremental quantity of discharged oil at said time $t_1$, said first divider providing said analog signal indicative of said incremental quantity;

a delay for delaying said analog signal that indicates said incremental quantity of discharged oil at said time $t_1$ for a period of time $(t_1 - t_2)$ required for said tanker to travel a predetermined distance;

a second multiplier for multiplying the delayed analog signal indicative of said incremental quantity of discharged oil at said time $t_1$ by another navigating velocity at said time $t_2$ to correct said delayed signal indicative of said incremental quantity at said time $t_1$ to a signal indicative of the instantaneous rate of discharge of oil at said time $t_1$ at said another velocity at said time $t_2$;

a subtractor for providing an output signal indicative of subtracting said signal indicative of said instantaneous rate of discharge of oil at said time $t_1$ at said another velocity at said time $t_2$ obtained by said correction from said first multiplier output signal indicative of said instantaneous rate of discharge of oil at said time $t_2$ said subtracting occuring when said output signals from said first and second multipliers are obtained by said subtractor; and an integrator for integrating said output signal from said subtractor to obtain the quantity of oil discharged from the travelling tanker within said predetermined distance within said time period $(t_1 - t_2)$.

2. An apparatus according to claim 1, wherein said delay includes:

a V-F converter for converting a velocity signal from a speedometer which measures said navigating velocity of said tanker to a pulse signal having a frequency corresponding to said velocity;

an A-D converter for dividing said analog signal indicative of said incremental quantity of discharged oil by said pulse signal from said V-F converter thereby digitizing said analog signal;

a shift register for outputting said digitized analog signal from said A-D converter in response to a given number of shift pulses supplied by said A-D converter in response to said V-F converter; and a D-A converter for multiplying the output from said shift register by said navigating velocity for analog conversion thereby reproducing said analog indicative signal of said incremental quantity of oil discharged.

3. An apparatus for determining the amount of oil in deballasting water and tank cleaning water that has been discharged from a travelling tanker during the navigation of a distance extending from a point of navigation at a time $t_1$ to another point of navigation at a time $t_2$ within a given distance backward of said another point of navigation, said apparatus comprising:

an oil meter for measuring the concentration of oil in said water at a first time $t_1$ and a second time $t_2$, said oil meter providing a signal indicative of said concentration;

a flow meter for measuring the flow rate of said water at said first time $t_1$ and said second time $t_2$, said flow meter providing a signal indicative of said flow rate;

a first multiplier for multiplying said concentration signal from said oil meter by said flow rate signal from said flow meter at said time, said multiplier supplying an output analog signal indicative of said instantaneous rate of discharge of oil at said time $t_1$ and at said time $t_2$;

a speedometer for supplying a signal indicative of a velocity of said tanker at said times $t_1 - t_2$;

a delay responsive to said signal indicative of said velocities and said analog signal indicative of said instantaneous rate of discharge of oil at said time $t_2$, said delay providing an output indicative of said instantaneous rate of discharge of oil at said time $t_1$ at said velocity at said time $t_2$;

a subtractor for providing an output signal indicative of subtracting said instantaneous rate of discharge of oil at said time $t_1$ at said velocity at said time $t_2$ from said instantaneous rate of discharge of oil at said time $t_2$, said subtracting occurring when said output signals from said delay and said multiplier are obtained by said subtractor; and an integrator for integrating said output signal from said subtractor to obtain the quantity of oil discharged from said travelling tanker within said predetermined distance within said time period $(t_1 - t_2)$.

4. An apparatus according to claim 3 wherein said delay includes:

a first V-F converter responsive to said signal indicative of said velocity of said tanker at said times, said first V-F converter providing a first pulse signal having a frequency corresponding to said signal indicative of said velocity;

an A-D converter for dividing said analog signal indicative of said instantaneous rate of discharge of said oil at said time $t_1$ by said first pulse signal at said time $t_1$, said A-D converter providing a digital signal representative of said analog signal;

a shift register responsive to said digital signal, said register shifting and outputting said digital signal in synchronism with said first pulse signal; and a D-A converter for multiplying the output from said shift register by said signal indicative of said velocity of said tanker at said time $t_2$ for analog conversion, thereby reproducing said analog signal indicative of said instantaneous rate of discharge of oil at said time $t_1$ at said velocity at said time $t_2$, 5. An apparatus according to claim 4 wherein said A-D converter includes:

a second V-F converter for converting said analog signal indicative of said instantaneous rate of discharge of oil at said time $t_1$ to a second pulse signal;

a pulse gate circuit for opening an associated gate in sychronization with said first pulse signal from said first V-F converter, said second pulse signal passing through said gate when open;

a counter circuit for counting the number of times said second pulse signal passes through said gate; and a memory for memorizing the number of pulses counted by said counter circuit, said counter circuit and said memory resetting in synchronism with said first pulse signal from said first V-F converter.

6. An apparatus for determining the amount of oil in deballasting water and tank cleaning water that has been discharged from a travelling tanker during the navigation of a distance extending from a point of navigation at a time $t_1$ to another point of navigation at a time $t_2$ within a given distance backward of said another point of navigation, said apparatus comprising:

an oil meter for measuring the concentration of oil in said water at a time $t_1$ and at a time $t_2$, said oil meter providing a signal indicative of said concentration;

a flow meter for measuring the flow rate of said water at said time $t_1$ and at said time $t_2$, said flow meter providing a signal indicative of said flow rate;

a speedometer for supplying a signal indicative of a velocity of said tanker at said times;

a multiplier-divider responsive to said oil concentration signal, said flow rate signal, and said velocity signal, said multiplier-divider multiplying said concentration signal at said time $t_1$ by said flow signal at said time $t_1$ to provide a output signal indicative of the instantaneous rate of discharge of oil at said time $t_1$, said multiplier-divider dividing said output signal indicative of said instantaneous rate of discharge of oil at said time $t_1$ by said velocity signal of said tanker at said time $t_1$ to provide an analog signal indicative of an incremental quantity of discharged oil at said time $t_1$;

a V-F converter for converting said velocity signal to a pulse signal having a frequency corresponding to said velocity signal;

an A-D converter responsive to said pulse signal and said analog signal indicative of said incremental quantity of discharged oil at said time $t_1$, said A-D converter providing a digital signal output indicative of said analog signal indicative of said incremental quantity of discharged oil at said time $t_1$;

a delay circuit responsive to said signal pulse and said digital signal at said time $t_2$, said delay circuit delaying said digital signal indicative of said incremental quantity of oil at said time $t_1$ for a period of time ($t_1 - t_2$) required for said tanker to travel a predetermining distance; and an adder-subtractor responsive to a corresponding digital signal at said time $t_2$ and said delayed digital signal at said time $t_1$, said adder-subtractor subtracting said digital signals from each other in response to said pulse signal, said adder-subtractor summing the differences generated by said subtracting to provide a signal indicative of the total amount of oil discharged within said period of time.

7. An apparatus according to claim 6 wherein said signal indicative of said incremental quantity of discharged oil at said time $t_1$ that has been digitized by said A-D converter is inputted to said adder-subtractor after said signal of incremental quantity at time $t_1$ has been delayed for a period of time required for said tanker to travel said predetermined distance.

8. An apparatus according to claim 7 wherein said delay includes a shift register wherein said signal indicative of said incremental quantity of discharged oil at said time $t_1$ digitized by said A-D converter is inputted to said adder-subtractor when a number of shift pulses synchronized with said pulse signal from said V-F converter has reached a given number.

9. An apparatus according to claim 7 wherein said delay includes a shift register in which said digital signal of incremental quantity of discharged oil at said time $t_1$ is inputted to said adder-subtractor in response to the generation of said pulse signal from said V-F converter.

10. An apparatus according to claim 6 wherein said delay includes a shift register wherein said signal indicative of incremental quantity of discharged oil at said time $t_1$ digitized by said A-D converter is inputted to said adder-subtractor when a number of shift pulses synchronized with said pulse signal from said V-F converter has reached a given number.

11. An apparatus according to claim 6 wherein said delay includes a shift register in which said digital signal of incremental quantity of discharged oil at said time $t_1$ is inputted to said adder-subtractor in response to the generation of said pulse signal from said V-F converter.

* * * * *